(12) United States Patent  (10) Patent No.: US 7,129,276 B2
Ferrari                    (45) Date of Patent:     Oct. 31, 2006

(54) COMPOSITION COMPRISING AT LEAST ONE LIQUID FATTY PHASE STRUCTURED BY AT LEAST ONE SEMI-CRYSTALLINE POLYMER

(75) Inventor: Véronique Ferrari, Maisons-Alfort (FR)

(73) Assignee: L'Oreal S.A., Paris (FR)

( * ) Notice: Subject to any disclaimer, the term of this patent is extended or adjusted under 35 U.S.C. 154(b) by 103 days.

(21) Appl. No.: 10/138,326

(22) Filed: May 6, 2002

(65) Prior Publication Data

Related U.S. Application Data

(60) Provisional application No. 60/294,977, filed on Jun. 4, 2001.

(30) Foreign Application Priority Data

May 4, 2001 (FR) .................................. 01 06046

(51) Int. Cl.
*A61K 7/00* (2006.01)
*A61K 7/027* (2006.01)
*A61K 7/031* (2006.01)
*A61K 7/032* (2006.01)

(52) U.S. Cl. .................................. 514/772.3

(58) Field of Classification Search ............. 514/772.3, 514/772.4, 772.6, 784, 844
See application file for complete search history.

(56) References Cited

U.S. PATENT DOCUMENTS

| 4,057,622 A | * | 11/1977 | Hase et al. | 514/772.5 |
| 4,057,623 A | * | 11/1977 | Hase et al. | 514/772.5 |
| 5,156,911 A | | 10/1992 | Stewart | |
| 5,302,380 A | | 4/1994 | Castrogiovanni et al. | |
| 5,519,063 A | | 5/1996 | Mondet et al. | |
| 5,736,125 A | * | 4/1998 | Morawsky et al. | 424/59 |
| 6,180,123 B1 | * | 1/2001 | Mondet | 424/401 |

FOREIGN PATENT DOCUMENTS

| DE | 19523478 C1 | * 12/1996 |
| DE | 19524210 A1 | * 1/1997 |
| EP | 0 550 745 | 7/1993 |
| EP | 0 951 897 | 10/1999 |
| EP | 951897 A2 | * 10/1999 |
| EP | 1 034 776 | 9/2000 |
| WO | WO 01/19333 | 3/2001 |

OTHER PUBLICATIONS

B. Boutevin et al., "Study of morphological and mechanical properties of PP/PBT blends," Polymer Bulletin, vol. 34, No. 1, Jan. 1995, pp. 117-123.
Pratima Rangarajan et al., "Morphology of Semicrystalline Block Copolymers of Ethylene-(Ethylene-alt-propylene)," Macromolecules, vol. 26, No. 17, Aug. 16, 1993, pp. 4640-4645.
D. Richter et al., "Polymer Aggregates with Crystalline Cores: The System Polyethylene-Poly(ethylenepropylene)," Macromolecules, vol. 30, No. 4, Feb. 24, 1997, pp. 1053-1068.
I. W. Hamley, "Crystallization in Block Copolymers," Advances in Polymer Science, vol. 148, 1999, pp. 113-137.
Shuichi Nojima et al., "Melting Behavior of Poly(e-caprolactone)-block-Polybutadiene Copolymers," Macromolecules, vol. 32, No. 11, Jun. 1, 1999, pp. 3727-3734.
English language Derwent Abstract of EP 1 034 776, Sep. 13, 2000.

* cited by examiner

*Primary Examiner*—Kelechi C. Egwim
(74) *Attorney, Agent, or Firm*—Finnegan, Henderson, Farabow, Garrett & Dunner L.L.P.

(57) ABSTRACT

A composition comprising, in a physiologically acceptable medium, at least one liquid fatty phase structured by at least one semi-crystalline polymer having an organic structure, wherein said polymer is solid at ambient temperature; and particles that are solid at ambient temperature and are dispersed in said medium, wherein the particles can be introduced into the medium in the form of a colloidal dispersion. This composition can be provided in the form of a stick which deposits, on a kerations substance, such as the lips, a glossy, nonsticky, and covering film.

63 Claims, No Drawings

COMPOSITION COMPRISING AT LEAST ONE LIQUID FATTY PHASE STRUCTURED BY AT LEAST ONE SEMI-CRYSTALLINE POLYMER

This application claims priority of U.S. Provisional Application No. 60/294,977, filed Jun. 4, 2001.

The present invention relates to a composition for caring for and/or treating and/or making up the skin, including the scalp, and/or the lips of the face of human beings which comprises a liquid fatty phase structured by at least one specific polymer and can be provided in the form of a stick of lipstick, the application of which results in a glossy, covering and nonsticky deposit.

It is commonplace, in cosmetic or dermatological products, to find a structured, namely stiffened, liquid fatty phase; this is particularly the case in solid compositions, such as deodorants, lip balms, lipsticks, concealers and cast foundations. This structuring is obtained using solid particles or fillers, and waxes. Unfortunately, these fillers or waxes have a tendency to render the composition matt, which is not always desirable, such as for a lipstick; this is because women are always looking for a lipstick in the stick form which deposits an ever glossier film.

In accordance with the present invention, the phrase "liquid fatty phase" is understood to mean a fatty phase which is liquid at ambient temperature (25° C.) and atmospheric pressure (760 mm of Hg) and which comprises one or more fatty substances which are liquid at ambient temperature, also known as oils, and which are compatible with one another. This fatty phase is macroscopically homogeneous.

The structuring of the liquid fatty phase makes it possible to limit its exudation from solid compositions and, furthermore, to limit, after deposition on the skin or lips, its migration over time into the wrinkles and fine lines, which is desired for a lipstick. The term "migration" is understood to mean overflowing of the composition and the color from the initial outline. Significant migration of the liquid fatty phase, laden with coloring materials, leads to an unsightly effect around the lips, particularly accentuating the wrinkles and fine lines. This migration is often mentioned by women as a major failing of conventional lipsticks. Furthermore, the fillers make it possible to reduce the sticky feel of some oils, such as castor oil or polyisobutenes, generally used in lipsticks.

The gloss is essentially related to the nature of the liquid fatty phase. Thus, it is possible to reduce the level of fillers and waxes in the composition in order to increase the gloss of a lipstick, but then the migration of the liquid fatty phase and/or the sticky feel of the composition increase. In other words, the level of fillers and/or of waxes necessary for the preparation of a cosmetically acceptable stick is a brake on the gloss of the layer.

One aspect of the present invention relates to the manufacture of a stick, and, more generally, of a composition which is solid at ambient temperature, comprising little or nothing in the way of fillers and/or little or nothing in the way of waxes, such as those used conventionally in cosmetics.

Accordingly, the present invention relates to substituting all or a portion of the fillers and/or waxes conventionally used in cosmetic compositions by semi-crystalline polymers which are solid at ambient temperature and which have an organic structure. There is an attendant difficulty of introducing solid particles, such as colored particles, which are insoluble in the medium of these compositions, such as pigments and pearlescent agents.

It has been found that, above a few percent of solid particles, they can later flocculate and aggregate, thus rapidly destabilizing the compositions at ambient temperature. This can be troublesome when the composition is in, for example, the solid form. In addition, the distribution of these particles in the composition may not be homogeneous, conferring a grainy appearance and feel; this can be troublesome when the composition is, for example, a makeup product. This is because such makeup obtained is nonuniform and unsightly, accentuating the flaws of the substrate and of the skin, which is entirely the reverse of what is desired by the consumer. This flocculation is partially due to an excessively slow rate of structuring (and more especially of gelling) of the liquid fatty phase by these semi-crystalline polymers and at the very least slower than that obtained with waxes.

One aspect of the invention is a composition for caring for and/or making up and/or treating Kerations substances, such as the skin and/or lips of the face and/or superficial body growths, which makes it possible to overcome at least one of these disadvantages.

One aspect of the invention is a composition comprising, in a physiologically acceptable medium: (i) at least one liquid fatty phase structured by at least one semi-crystalline polymer having an organic structure, wherein said semi-crystalline polymer is solid at ambient temperature; and (ii) particles that are solid at ambient temperature; and (iii) at least one dispersing agent in an amount sufficient to disperse said particles in said medium.

Another aspect of the invention is a product for making up a Kerations substance comprising, in a physiologically acceptable medium, (i) at least one liquid fatty phase structured by at least one semi-crystalline polymer having an organic structure, wherein said semi-crystalline polymer is solid at ambient temperature; and (ii) colored particles that are solid at ambient temperature; and (iii) at least one dispersing agent in an amount sufficient to disperse said colored particles in said medium.

Yet another aspect of the invention is a cosmetic process for caring for, making up, or treating a Kerations substance of a human being, comprising applying an effective amount of a composition comprising, in a physiologically acceptable medium: (i) at least one liquid fatty phase structured by at least one semi-crystalline polymer having an organic structure, wherein said semi-crystalline polymer is solid at ambient temperature; and (ii) particles that are solid at ambient temperature; and (iii) at least one dispersing agent in an amount sufficient to disperse said particles in said medium.

Another aspect of the invention is a process of making a cosmetic composition comprising a physiologically acceptable medium, comprising including in said medium (i) at least one semi-crystalline polymer that has an organic structure and is solid at ambient temperature, (ii) particles that are solid at ambient temperature and are dispersed in said medium; and (iii) at least one dispersing agent in an amount effective to disperse said particles in said medium.

Another aspect of the invention is a process of using a colloidal dispersion of solid particles in a cosmetic composition comprising, in a physiologically acceptable medium, at least one liquid fatty phase structured by at least one semi-crystalline polymer, said at least one semi-crystalline polymer having an organic structure and being solid at ambient temperature, comprising including in said cosmetic composition a colloidal dispersion of particles in said composition, wherein the particles are solid at ambient temperature.

Another aspect of the invention is a process for coloring and/or stabilizing a cosmetic composition comprising, in a physiologically acceptable medium, at least one liquid fatty phase structured by at least one semi-crystalline polymer, said semi-crystalline polymer having an organic structure and being solid at ambient temperature, comprising including in said cosmetic composition a colloidal dispersion of colored particles that are solid at ambient temperature in said composition.

Another aspect of the invention is a method for stabilizing a cosmetic composition and/or producing a stable cosmetic composition comprising: including, in a cosmetic composition comprising, in a physiologically acceptable medium, at least one liquid fatty phase structured by at least one semi-crystalline polymer that has an organic structure and is solid at ambient temperature and colored particles that are solid at ambient temperature, comprising including a dispersing agent in said composition in an amount effective for dispersing said colored particles.

Another aspect of the invention is a composition comprising, in a physiologically acceptable medium: (i) at least one liquid fatty phase structured by at least one semi-crystalline polymer that has an organic structure, wherein said semi-crystalline polymer is solid at ambient temperature; and (ii) particles that are solid at ambient temperature; and (iii) at least one dispersing agent in an amount sufficient to disperse said particles in said medium; wherein said semi-crystalline polymer does not comprise a polysaccharide backbone.

Surprisingly, it has been found that the use of semi-crystalline polymers in combination with solid particles and at least one dispersing agent, even in the absence of conventional wax and/or of filler, makes it possible to obtain a stable stick, such as for using in making up, the application of which can result in a colored, uniform, glossy and nonsticky film which has good coverage and which does not migrate, with restriction of the sedimentation of the particles, colored particles for instance, at the end of the stick.

The invention applies not only to products for making up the lips but also to products for caring for and/or treating the lips, such as balms, and the skin, including the scalp, such as daily care creams, products for coloring the skin and products for the antisun protection of the skin of the face, to products for making up the skin, both of the human face and of the human body, such as foundations, such as those cast as a stick or in a dish, concealers and temporary tattooing products, to body hygiene products, such as deodorants, or stick deodorants, and to products for making up the eyes, such as eyeliners, such as those in the pencil form, and mascaras, such as those in the cake form.

More specifically, one aspect of the invention is a composition comprising a physiologically acceptable medium comprising at least one liquid fatty phase structured by at least one semi-crystalline polymer with an organic structure which is solid at ambient temperature and particles which are solid at ambient temperature and which are dispersed in said medium using at least one dispersing agent.

For example, the solid particles can be introduced into the medium in the form of a colloidal dispersion of said particles.

The composition of the invention can be provided in the form of a paste, solid, or cream. It can be an oil-in-water or water-in-oil emulsion or a solid or soft anhydrous gel. It can be provided in the anhydrous form or in the form of an anhydrous gel, such as a stick or in a dish.

The term "semi-crystalline polymer" is understood to mean, within the meaning of the invention, polymers comprising a crystallizable part, a pendent chain or a block in the backbone, and an amorphous part and exhibiting a first-order reversible phase change temperature, such as a melting temperature (solid-liquid transition). The term "polymers" is understood to mean, within the meaning of the invention, compounds comprising at least two repeat units, such as at least 3 repeat units and further such as at least 10 repeat units. When the crystallizable part is a block of the polymer backbone, this crystallizable block is different in chemical nature from that of the amorphous blocks; the semi-crystalline polymer is, in this case, a block polymer, for example of the diblock, triblock or multiblock type. The term "block" is understood to mean generally at least 5 identical repeat units. The crystallizable block or blocks are then different in chemical nature from the amorphous block or blocks.

U.S. Pat. No. 5,302,380 (DA) discloses cosmetic compositions for improved adhesion to the skin comprising atactic polypropylene homopolymers with a crystallinity of 0.1 to 15% and with a molecular weight of approximately 1,000 to 10,000. These polymers comprise neither a crystallizable pendent chain nor a crystallizable block. Their atactic arrangement, namely irregular arrangement, does not normally make crystallization possible. In addition, these polymers provide no discernible structuring of the compositions comprising them.

The composition can comprise one or more semi-crystalline polymers with an organic structure and, for example, at least one semi-crystalline polymer with a low melting point (also known as second polymer), in combination with at least one semi-crystalline polymer with a high melting point (also known as first polymer). These polymers can exhibit a melting temperature greater than the temperature of the Keratinons substrate intended to receive the composition such as the lips or the skin, including the scalp. According to the invention, a semi-crystalline polymer with a low melting point is a semi-crystalline polymer with a melting temperature of less than 50° C. and a semi-crystalline polymer with a high melting point is a semi-crystalline polymer with a melting temperature at least equal to 50° C.

This melting temperature can be measured by any known method, such as by using a differential scanning colorimeter (D.S.C).

The semi-crystalline polymers to which the invention applies can comprise a) a polymer backbone and b) at least one crystallizable organic side chain and/or at least one crystallizable organic block forming part of the polymer backbone.

The semi-crystalline polymer or polymers to which the invention applies can exhibit a number-average molecular mass of greater than 2,000. The semi-crystalline polymers with a high melting point which can be used in the invention can be semi-crystalline polymers with an organic structure which are solid at ambient temperature and which have a melting temperature of greater than or equal to 50° C., comprising a) an organic polymer backbone and b) at least one crystallizable organic side chain and/or at least one crystallizable organic block forming part of the polymer backbone, said polymer having a number-average molecular mass of greater than 2,000.

The combination of one or more polymers with a high melting point, and in general of one or more compounds with a high melting point, with one or more compounds with a low melting point, such as one or more semi-crystalline polymers with a low melting point, makes it possible to confer, on the composition, good stability over time and with temperature. Thus, it is possible to obtain a composition which remains macroscopically homogeneous without exudation of the liquid fatty phase, even in a moist atmosphere, for at least 2 months at 45° C. and atmospheric pressure.

Furthermore, the properties of nonmigration of the composition into the wrinkles and fine lines of the skin, such as around the lips, but also into the folds of the upper eyelid and around the eyes, are improved.

Mention may be made, as another compound with a high melting point which can be used in the invention, of waxes with a high melting point ($\geq 50°$ C.), such as some polyethylene waxes, for example Epolene N-14, sold by Eastman Chemical Co.; carnauba waxes; and some microcrystalline waxes, such as those sold by Tisco under the trade name "Tisco wax 88"; and semi-crystalline polymers. However, it is possible to use, as a compound with a high melting point, crystalline polymers which are solid at ambient temperature and which have a melting temperature of greater than 50° C., random polymers comprising controlled crystallization, as disclosed in the document (D1) EP-A-0 951 897 9 (the disclosure of which is incorporated by reference herein), or the commercial products Engage 8 401 and Engage 8 402 from Dupont de Nemours, with melting temperatures of 51° C. and 64° C. respectively, which are random ethylene/1-octene bipolymers.

Semi-crystalline Polymers

For example, the semi-crystalline polymer or polymers (with a high or low melting point) of the composition of the invention comprise a number-average molecular mass $\overline{M}n$ ranging from 2,000 to 800,000, such as from 3,000 to 500,000, for example from 4,000 to 150,000. According to another aspect of the invention, the number-average molecular mass $\overline{M}n$ ranges from 4,000 to 99,000.

The semi-crystalline polymer or polymers according to the invention acting as structuring agents are solids which are nondeformable at ambient temperature (25° C.) and atmospheric pressure (760 mm of Hg). They are capable of structuring, alone or as a mixture, the composition without addition of a specific surfactant, filler, or wax.

According to the invention, the semi-crystalline polymers with a low melting point and/or the polymers or compounds with a high melting point are soluble to at least 1% by weight in the fatty phase at a temperature greater than their melting temperature. Apart from the crystallizable chains or blocks, the blocks of the polymers are amorphous. The term "crystallizable chain or block" is understood to mean, within the meaning of the invention, a chain or block which, if it were alone, would change reversibly from the amorphous state to the crystalline state, according to whether the temperature is above or below the melting temperature. A chain within the meaning of the invention is a group of atoms which is in the pendent or side position with respect to the backbone of the polymer. A block is a group of atoms belonging to the backbone, a group constituting one of the repeat units of the polymer.

The polymer backbone of the semi-crystalline polymers can be soluble in the liquid fatty phase.

According to the invention, the semi-crystalline compound or compounds with a high melting point can be polymers having a melting temperature $M.p._1$ such that $50°$ C.$\leq M.p._1 \leq 150°$ C., such as $55°$ C.$\leq M.p._1 \leq 150°$ C. and further such as $60°$ C.$\leq M.p._1 \leq 130°$ C. and the polymers with a low melting point may have a melting temperature $M.p._2$ such that $30°$ C.$\leq M.p._2 \leq 50°$ C., such as $35°$ C.$\leq M.p._2 \leq 45°$ C. This melting temperature is a first-order state change temperature.

Generally, the polymers with a low melting point exhibit a melting temperature $M.p._2$ at least equal to the temperature of the Keratinons substrate which has to receive the composition according to the invention.

The crystallizable blocks or chains of the semi-crystalline polymers may represent at least 30% of the total weight of each polymer such as at least 40%. The semi-crystalline polymers of the invention with crystallizable blocks are block or multiblock polymers. They can be obtained by polymerization of a monomer with reactive double (or ethylenic) bonds or by polycondensation. When the polymers of the invention are polymers with crystallizable side chains, the latter can be in the statistical or random form.

The semi-crystalline polymers of the invention can be synthetic in origin. In addition, they may not comprise a polysaccharide backbone. Generally, the crystallizable units (chains or blocks) of the semi-crystalline polymers according to the invention originate from monomer(s) with crystallizable block(s) or chain(s) used for the manufacture of semi-crystalline polymers.

According to the invention, the semi-crystalline polymer with a low melting point and the semi-crystalline polymer with a high melting point are chosen from block copolymers comprising at least one crystallizable block and at least one amorphous block, homopolymers and copolymers carrying at least one crystallizable side chain per repeat unit, and mixtures thereof.

The semi-crystalline polymers which can, for example, be used in the invention are:

- block copolymers of polyolefins with controlled crystallization, the monomers of which are disclosed in D1,
- polycondensates, such as those of aliphatic or aromatic or aliphatic/aromatic polyester type,
- homo- or copolymers carrying at least one crystallizable side chain and homo- or copolymers carrying, in the backbone, at least one crystallizable block, such as those disclosed in (D2) U.S. Pat. No. 5,156,911 (the disclosure of which is incorporated by reference herein),
- homo- and copolymers carrying at least one crystallizable side chain with in particular fluorinated group(s), such as disclosed in document (D3) WO-A-01/19333 (the disclosure of which is incorporated by reference herein),
- and mixtures thereof. In the last two cases, the crystallizable side chain or block or side chains or blocks are hydrophobic.

A) Semi-crystalline Polymers with Crystallizable Side Chains

Mention may be made of those defined in the documents U.S. Pat. No. 5,156,911 and WO-A-01/19333.

These are homopolymers and copolymers comprising from 50% to 100% by weight of units resulting from the polymerization of one or more monomers carrying a crystallizable hydrophobic side chain.

These homo- and copolymers can have any nature provided that they exhibit at least the characteristic of being soluble or dispersible in the liquid fatty phase by heating above their melting temperature M.p. They can result:

from the polymerization, such as radical polymerization, of one or more monomers with reactive double bond(s) or ethylenic monomers with respect to polymerization, namely with a vinyl, (meth)acrylic or allyl group, from the polycondensation of one or more monomers carrying coreactive groups (carboxylic or sulfonic acid, alcohol, isocyanate or amine groups), such as, for example, polyesters, polyurethanes, polyethers, polyureas or polyamides.

a) Generally, the crystallizable units (chains or blocks) of the semi-crystalline polymers according to the invention originate from monomers with crystallizable block(s) or chain(s) used for the manufacture of semi-crystalline polymers. These polymers can be chosen from the homopolymers and copolymers resulting from the polymerization of at least one monomer having crystallizable chain(s) which can be represented by the formula X:

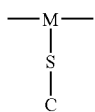

wherein M represents an atom of the polymer backbone, S represents a spacer, and C represents a crystallizable group.

The crystallizable chains "—S—C" can be aliphatic or aromatic and optionally fluorinated or perfluorinated. "S" can represent a linear or branched or cyclic $(CH_2)_n$ or $(CH_2CH_2O)_n$ or $(CH_2O)$ group with n an integer ranging from 0 to 22. For example, "S" is a linear group. Substituents "S" and "C" can be different, for instance.

When the crystallizable chains are hydrocarbonaceous aliphatic chains, they comprise hydrocarbonaceous alkyl chains with at least 11 carbon atoms and at most 40 carbon atoms such as at most 24 carbon atoms. They can be aliphatic chains or alkyl chains having at least 12 carbon atoms and can be $C_{14}$–$C_{24}$ alkyl chains. When they are fluorinated or perfluorinated alkyl chains, they comprise at least 11 carbon atoms, at least 6 carbon atoms of which are fluorinated.

The term "crystallizable chain" is understood to mean a chain comprising at least 6 carbon atoms.

Mention may be made, as examples of semi-crystalline polymers or copolymers with crystallizable chain(s), of those resulting from polymerization of one or more following monomers: saturated alkyl (meth)acrylates with the $C_{14}$–$C_{24}$ alkyl group; perfluoroalkyl (meth)acrylates with a $C_{11}$–$C_{15}$ perfluoroalkyl group; N-alkyl(meth)acrylamides with the $C_{14}$ to $C_{24}$ alkyl group, unsubstituted or substituted with at least one fluorine atom; vinyl esters with alkyl or perfluoro(alkyl) chains with the $C_{14}$ to $C_{24}$ alkyl group (with at least 6 fluorine atoms per one perfluoroalkyl chain); vinyl ethers with alkyl or perfluoro(alkyl) chains with the $C_{14}$ to $C_{24}$ alkyl group and at least 6 fluorine atoms per one perfluoroalkyl chain; $C_{14}$ to $C_{24}$ α-olefins, such as, for example, octadecene; para-alkylstyrenes with an alkyl group comprising from 12 to 24 carbon atoms; and mixtures thereof.

When the polymers result from a polycondensation, the crystallizable hydrocarbonaceous and/or fluorinated chains as defined above are carried by a monomer which can be a diacid, a diol, a diamine or a diisocyanate.

When the polymers which are the subject-matter of the invention are copolymers, they additionally comprise from 0 to 50% of Y or Z groups resulting from the copolymerization:

α) of Y, which is a polar or nonpolar monomer or a mixture of the two:

When Y is a polar monomer, it is either a monomer carrying polyoxyalkylenated groups (such as oxyethylenated and/or oxypropylenated groups), a hydroxyalkyl (meth)acrylate, such as hydroxyethyl acrylate, (meth)acrylamide, an N-alkyl(meth)acrylamide, an N,N-dialkyl(meth)acrylamide, such as, for example, N,N-diisopropylacrylamide or N-vinylpyrrolidone (NVP), N-vinylcaprolactam, or a monomer carrying at least one carboxylic acid group, such as (meth)acrylic acid, crotonic acid, itaconic acid, maleic acid or fumaric acid, or carrying a carboxylic acid anhydride group, such as maleic anhydride, and mixtures thereof.

When Y is a nonpolar monomer, it can be an ester of the linear, branched or cyclic alkyl (meth)acrylate type, a vinyl ester, an alkyl vinyl ether, an α-olefin, styrene or styrene substituted by a $C_1$–$C_{10}$ alkyl group, such as α-methylstyrene, or a macromonomer of the polyorganosiloxane type with vinyl unsaturation.

The term "alkyl" is understood to mean, in accordance with the present invention, a saturated group, such as a $C_8$ to $C_{24}$ group, unless specifically mentioned.

β) of Z, which is a polar monomer or a mixture of polar monomers. In this case, Z has the same definition as the "polar Y" defined above.

The semi-crystalline polymers with a crystallizable side chain can be alkyl (meth)acrylate or alkyl(meth)acrylamide homopolymers with an alkyl group as defined above or a $C_{14}$–$C_{24}$ alkyl group, copolymers of these monomers with a hydrophilic monomer, which can be different in nature from (meth)acrylic acid, such as N-vinylpyrrolidone or hydroxyethyl (meth)acrylate, and mixtures thereof.

B) Polymers Carrying, in the Backbone, at Least One Crystallizable Block

These are again polymers which are soluble or dispersible in the liquid fatty phase by heating above their melting point M.p. These polymers can be block copolymers composed of at least two blocks of different chemical natures, one of which is crystallizable.

Use may be made of the block polymers defined in U.S. Pat. No. 5,156,911,

Block copolymers of olefin or of cycloolefin with a crystallizable chain, such as those resulting from the block polymerization of:

cyclobutene, cyclohexene, cyclooctene, norbornene (that is to say, bicyclo[2.2.1]hept-2-ene), 5-methyl norbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene or mixtures thereof, with ethylene, propylene, 1-butene, 3-methyl-1-butene, 1-hexene, 4-methyl-1-pentene, 1-octene, 1-decene, 1-icosene or mixtures thereof, block copoly(ethylene/norbornene)s and (ethylene/propylene/ethylidenenorbornene) block terpolymers. Use may also be made of those resulting from the block copolymerization of at least 2 $C_2$–$C_{16}$ α-olefins, such as $C_2$–$C_{12}$ α-olefins, such as those mentioned above, and can be the block bipolymers of ethylene and 1-octene.

The copolymers can be copolymers exhibiting at least one crystallizable block, the remainder of the copolymer being amorphous (at ambient temperature). These copolymers can, in addition, exhibit two crystallizable blocks of different chemical natures. The copolymers can have, at ambient temperature, both a crystallizable block and a both hydrophobic and lipophilic amorphous block which are sequentially distributed; mention may be made, for example, of the polymers having one of the following crystallizable blocks and one of the following amorphous blocks:

Block crystallizable by nature: a) polyester, such as poly(alkylene terephthalate)s, b) polyolefin, such as polyethylenes or polypropylenes.

Amorphous and lipophilic block, such as: amorphous polyolefins or copoly(olefin)s, for example poly(isobutylene), hydrogenated polybutadiene, hydrogenated poly(isoprene) or copoly(ethylene/propylene).

Mention may be made, as examples of such copolymers with a distinct crystallizable block and with a distinct amorphous block, of:

α) poly(ε-caprolactone)-b-poly(butadiene) block copolymers with butadiene, such as those used hydrogenated, such as those described in the article D4, "Melting behavior of poly(-caprolactone)-block-polybutadiene copolymers", by S. Nojima, Macromolecules, 32, 3727–3734 (1999) (the disclosure of which is incorporated by reference herein).

β) Block or multiblock hydrogenated poly(butylene terephthalate)-b-poly(isoprene) block copolymers, cited in the article D5, "Study of morphological and mechanical properties of PP/PBT", by B. Boutevin et al., Polymer Bulletin, 34, 117–123 (1995) (the disclosure of which is incorporated by reference herein).

γ) The poly(ethylene)-b-copoly(ethylene/propylene) block copolymers cited in the articles D6, "Morphology of semi-crystalline block copolymers of ethylene-(ethylene-alt-propylene)", by P. Rangarajan et al., Macromolecules, 26, 4640–4645 (1993) and D7, "Polymer aggregates with crystalline cores: the system poly(ethylene)-poly(ethylene-propylene)", by P. Richter et al., Macromolecules, 30, 1053–1068 (1997) (the disclosures of which are incorporated by reference herein).

δ) The poly(ethylene)-b-poly(ethylethylene) block copolymers cited in the general article D8, "Crystallization in block copolymers", by I. W. Hamley, Advances in Polymer Science, vol. 148, 113–137 (1999) (the disclosure of which is incorporated by reference herein).

The semi-crystalline polymers of the composition of the invention may or may not be partially crosslinked provided that the degree of crosslinking is not harmful to their dissolution or dispersion in the liquid fatty phase by heating above their melting temperature. The crosslinking can then be chemical crosslinking, by reaction with a multifunctional monomer during the polymerization. It can also be physical crosslinking, which can then be due either to the establishment of bonds of hydrogen or dipolar type between groups carried by the polymer, such as, for example, dipolar interactions between carboxylate ionomers, these interactions being low in degree and carried by the backbone of the polymer, or to phase separation between the crystallizable blocks and the amorphous blocks carried by the polymer.

The semi-crystalline polymers of the composition according to the invention can be un-crosslinked.

Mention may be made, as a non-limiting example of structuring semi-crystalline polymers which can be used in the composition according to the invention, of the Intelimer® products from Landec described in the brochure D9 "Intelimer® polymers", Landec IP22 (Rev. 4–97) (the disclosure of which is incorporated by reference herein). These polymers are in the solid form at ambient temperature (25° C.). They carry crystallizable side chains and exhibit the above formula X.

i) The semi-crystalline polymers with a low melting point are in particular those disclosed in examples 3, 4, 5, 7 and 9 of U.S. Pat. No. 5,156,911 comprising a —COOH group, resulting from the copolymerization of acrylic acid and of $C_5$ to $C_{16}$ alkyl (meth)acrylate with an $M.p._2$ ranging from 20° C. to 35° C. or from the copolymerization:

of acrylic acid, of hexadecyl acrylate and of isodecyl acrylate in a 1/16/3 ratio,
of acrylic acid and of pentadecyl acrylate in a 1/19 ratio,
of acrylic acid, of hexadecyl acrylate and of ethyl acrylate in a 2.5/76.5/20 ratio,
of acrylic acid, of hexadecyl acrylate and of methyl acrylate in a 5/85/10 ratio,
of acrylic acid and of polyoctadecyl methacrylate in a 2.5/97.5 ratio.

Use may also be made of the polymer referenced Structure "O" from National Starch, such as that disclosed in U.S. Pat. No. 5,736,125 (D10) (the disclosure of which is incorporated by reference herein) with an $M.p._2$ of 44° C., and of semi-crystalline polymers with crystallizable pendent chains comprising fluorinated groups, such as disclosed in Examples 1, 4, 6, 7 and 8 of WO-A-01/19333.

Use may also be made of the semi-crystalline polymers with a low melting point obtained by copolymerization of stearyl acrylate and of acrylic acid or of NVP, as disclosed in the document U.S. Pat. No. 5,519,063 (D11) or EP-A-0 550 745 (D12) (the disclosures of which are incorporated by reference herein), and as well as those described in the polymer preparation Examples 1 and 2 below, with melting temperatures of 40° C. and 38° C. respectively.

ii) The semi-crystalline polymers with a high melting point such as the Intelimer described in document D9, with a melting temperature $M.p._1$ of 56° C., which is a product which is viscous at ambient temperature, impermeable and nonsticky.

Use may also be made of the semi-crystalline polymers obtained by copolymerization of behenyl acrylate and of acrylic acid or of NVP as disclosed in the documents D11 and D12 or those described in the polymer preparation Examples 3 and 4 below, with melting temperatures of 60° C. and 58° C. respectively.

The semi-crystalline polymers with a low melting point and/or those with a high melting point may not comprise a carboxyl group.

The gelling of the fatty phase can be adjusted according to the nature of the polymers and their respective concentrations and can be such that a rigid structure in the form of a stick is obtained.

The level of each polymer is chosen according to the desired hardness of the composition and according to the specific application envisaged. The respective amounts of polymer can be such that they make it possible to obtain a solid which can disintegrate, exhibiting a hardness ranging from 100 to 350 gf, for example. This hardness can be measured by the "cheese wire" method, which comprises cutting a stick of lipstick with a diameter of 12.7 mm and in measuring the hardness at 20° C. by means of a DFGHS 2 dynamometer from Indelco-Chatillon moving at a rate of 100 mm/minute. It is expressed as the shear force (expressed in gram-force) needed to cut a stick under these conditions.

This hardness is such that the composition is self-supporting and can easily disintegrate to form a satisfactory layer on the skin and the lips. In addition, with this hardness, the composition of the invention in the cast form, such as a stick, possesses good impact strength.

The composition of the invention can be provided in the form of a solid stick with a hardness ranging from 100 gf to 350 gf, measured according to the "cheese wire" method. However, it is possible to use an amount of semi-crystalline polymer such that the composition is in the form of a soft paste which can be applied with a finger or using an applicator to Keratinons substances.

In practice, the total amount of semi-crystalline polymer represents, for example, from 0.1 to 80% of the total weight of the composition, such as from 0.5 to 40% and further such as from 3 to 30%. In an example, the total amount of semi-crystalline polymer represents more than 10% by weight of the composition.

According to the invention, the semi-crystalline or crystalline compound with a high melting point and that with a low melting point are, for example, in a ratio by weight ranging from 10/90 to 90/10 such as from 40/60 to 60/40.

The ratio by weight of semi-crystalline polymer with an organic structure with respect to the liquid fatty phase is from 0.20 to 0.60 such as from 0.25 to 0.50, to obtain a hard stick which disintegrates on contact with the skin or lips and may have a hardness ranging from 100 to 350 gf.

The sticks according to the invention, when they are colored, make it possible, after application, to obtain a glossy and nonsticky layer which is homogeneous in color and which has good coverage (that is to say that the skin or lips do not appear under the makeup).

The Liquid Fatty Phase

The liquid fatty phase, structured by the semi-crystalline polymers with a low melting point and/or the semi-crystalline polymers with a high melting point, can constitute the continuous phase of the composition. This fatty phase can comprise one or more nonpolar or polar oils or a mixture of nonpolar oil(s) and of polar oil(s).

The nonpolar oils according to the invention can be silicone oils, such as linear or cyclic polydimethylsiloxanes (PDMSs) which are liquid at ambient temperature; polydimethylsiloxanes comprising pendent alkyl, alkoxy or phenyl groups and/or alkyl, alkoxy or phenyl groups at the end of the silicone chain, which groups have from 2 to 24 carbon atoms and which polydimethylsiloxanes are liquid at ambient temperature; liquid phenylated silicones, such as phenyl trimethicones, phenyl dimethicones, phenyl-trimethylsiloxydiphenylsiloxanes, diphenyl dimethicones, diphenylmethyldiphenyltrisiloxanes or (2-phenylethyl)trimethylsiloxysilicates; liquid linear or branched hydrocarbons or fluorocarbons of synthetic or mineral origin, such as liquid paraffins and their derivatives, liquid petrolatum, polydecenes, hydrogenated polyisobutene, such as Parleam® (hydrogenated isoparaffin), sold by Nippon Oil Fatts, isoparaffins or squalane; or mixtures thereof. The nonpolar oils used can be liquid nonpolar oils of the hydrocarbonaceous type of mineral or synthetic origin and can, for example, be chosen from Parleam® oil (hydrogenated isoparaffin), isoparaffins, squalane, and mixtures thereof. The liquid fatty phase can comprise at least one hydrocarbonaceous oil of mineral or synthetic origin.

The term "hydrocarbonaceous oil" is understood to mean, within the meaning of the invention, oils predominantly comprising carbon atoms and hydrogen atoms such as alkyl or alkenyl chains, such as alkanes or alkenes, but also oils with an alkyl or alkenyl chain comprising one or more ether, ester, hydroxyl or carboxylic acid groups.

It is possible to add polar oils to the nonpolar oils, the nonpolar oils acting as cosolvent for the polar oils, for example.

Nonlimiting examples of the polar oils useful according to the present invention include:

hydrocarbonaceous vegetable oils with a high content of triglycerides composed of esters of ($C_8$ to $C_{24}$) fatty acids and of glycerol, the fatty acids of which can have various chain lengths, it being possible for the chains to be linear or branched and saturated or unsaturated; these oils can be wheat germ, maize, sunflower, karite, castor, sweet almond, macadamia, apricot, soybean, rapeseed, cottonseed, alfalfa, poppy, pumpkinseed, sesame, cucumber, avocado, hazelnut, grape seed, blackcurrant seed, evening primrose, millet, barley, quinoa, olive, rye, safflower, candlenut, passionflower or musk rose oils; or triglycerides of caprylic/capric acids, such as those sold by Stearineries Dubois or those sold under the names Miglyol 810, 812 and 818 by Dynamit Nobel;

synthetic oils of formula $R_5COOR_6$ in which $R_5$ represents the residue of a linear or branched higher fatty acid comprising from 7 to 40 carbon atoms and $R_6$ represents a branched hydrocarbonaceous chain comprising from 3 to 40 carbon atoms, such as, for example, purcellin oil (cetearyl octanoate), isononyl isononanoate or $C_{12}$ to $C_{15}$ alkyl benzoate;

synthetic esters and ethers, such as isopropyl myristate, 2-ethylhexyl palmitate, octanoates, decanoates or ricinoleates of alcohols or of polyalcohols, hydroxylated esters, such as isostearyl lactate or diisostearyl malate; and pentaerythritol esters;

$C_8$ to $C_{26}$ fatty alcohols, such as oleyl alcohol;

fatty acids having from 12 to 22 carbon atoms, such as oleic acid, linoleic acid or linolenic acid;

and mixtures thereof.

The fatty phase can represent, in practice, from 5 to 99% of the total weight of the composition, such as from 20 to 80%. It may represent at least 60% of the total weight of the composition.

The Solid Particles

The composition additionally comprises particles which are solid at ambient temperature and which are dispersed in the physically acceptable medium of the composition, and in the structured liquid fatty phase, using a dispersing agent, for instance. These particles can be introduced into the composition in the form of a colloidal dispersion known as a "particulate paste". These particles can be chosen from pigments, pearlescent agents, fillers and mixtures thereof. These particles can be of any shape, such as spherical shape or elongate shape, such as fibers. They can be colored.

The term "particulate paste" is understood to mean, within the meaning of the invention, a concentrated colloidal dispersion of particles in a continuous medium, which particles are solid at ambient temperature (25° C.) and are coated or uncoated and which dispersion is stabilized using a dispersing agent or optionally without a dispersing agent. They are insoluble in the medium.

The colloidal dispersion is a suspension of particles of generally micronic size (<10 μm) in a continuous medium.

The fraction by volume of particles in a concentrated dispersion is from 20% to 40%, such as greater than 30%, which corresponds to a content by weight which can range up to 70%, according to the size of the particles.

The continuous medium of the paste can have any composition and can comprise any solvent or liquid fatty substance and mixtures thereof. The liquid medium of the particulate paste is one of the liquid fatty substances or oils which it is desired to use in the composition, thus forming part of the liquid fatty phase.

The particles dispersed in the medium can be composed of inorganic or organic particles or mixtures thereof, such as those described below.

The "particulate paste" can be a "pigmentary paste" comprising a colloidal dispersion of colored particles which may or may not be coated. These colored particles are pigments, pearlescent agents, or a mixture of pigments and pearlescent agents.

The pigments can be white or colored, inorganic and/or organic and coated or uncoated. Mention may be made, among inorganic pigments, of titanium dioxide, optionally treated at the surface, zirconium or cerium oxides, zinc, iron or chromium oxides (the iron oxides being black, yellow or red), manganese violet, ultramarine blue, chromium hydrate and ferric blue. Mention may be made, among organic pigments, of carbon black, pigments of D & C type, and lakes based on cochineal carmine or on barium, strontium, calcium or aluminum (such as D & C red 27, 21 or 7, D & C yellow 5 or 6, or F D & C blue No. 1). The pigments can represent from 0.1 to 50% as active material such as from 0.5 to 35% and further such as from 2 to 25% of the total weight of the composition.

The pearlescent pigments can be chosen from white pearlescent pigments, such as mica covered with titanium oxide or with bismuth oxychloride, colored pearlescent pigments, such as titanium oxide-coated mica with iron oxides, titanium oxide-coated mica with ferric blue or chromium oxide, or titanium oxide-coated mica with an organic pigment of the abovementioned type, and pearlescent pigments based on bismuth oxychloride. They can represent from 0 to 25% as active material (0.05 to 25%) of the total weight of the composition such as from 0.1 to 15% (if present).

The colloidal dispersion may represent from 0.1 to 60% by weight of the composition such as from 2 to 40% (if present).

The Dispersing Agent

The composition according to the invention comprises one or more dispersing agents which can be added independently of the solid particles or in the form of the colloidal dispersion of particles.

The dispersing agent serves to protect the dispersed particles against their agglomeration or flocculation. The concentration of dispersing agent generally used to satisfactorily disperse solid particles (without flocculation) and to stabilize a colloidal dispersion of particles is from 0.3 to 5 mg/m$^2$ of the particle surface area, for example from 0.5 to 4 mg/m$^2$ of the particle surface area. This dispersing agent can be a surfactant, an oligomer, a polymer or a mixture of several of them, carrying one or more functionalities having a high affinity for the surface of the particles to be dispersed. They can attach physically or chemically to the surface of the pigments. In addition, these dispersing agents can exhibit at least one functional group compatible with or soluble in the continuous medium. Use can be, for example, made of esters of poly(12-hydroxystearic acid), such as the stearate of poly(12-hydroxystearic acid) with a molecular weight of approximately 750 g/mol, such as that sold under the name of Solsperse 21 000 by Avecia, esters of poly(12-hydroxystearic acid) with polyols, such as glycerol or diglycerol, for example polyglyceryl-2 dipolyhydroxystearate (CTFA name), sold under the reference Dehymuls PGPH by Henkel (or diglyceryl poly(12-hydroxystearate)), or else poly(12-hydroxystearic acid), such as that sold under the reference Arlacel P100 by Uniqema, and mixtures thereof.

Mention may be made, as another dispersing agent which can be used in the composition of the invention, of quaternary ammonium derivatives of fatty acids which are polycondensed, such as Solsperse 17 000 sold by Avecia, or polydimethylsiloxane/oxypropylene mixtures, such as those sold by Dow Corning under the references DC2-5185 and DC2-5225 C.

Polydihydroxystearic acid and esters of poly(12-hydroxystearic acid) can be used for a hydrocarbonaceous or fluorinated medium, whereas oxyethylene/oxypropylenated dimethylsiloxane mixtures can be used for a silicone medium.

The Additives

The composition of the invention can additionally comprise any additive conventionally used in the field under consideration chosen from water, optionally thickened by an aqueous-phase thickener or gelling agent; coloring materials which are soluble in the medium; antioxidants; essential oils; preservatives; fragrances; pasty fatty substances or waxes other than the compounds with a high melting point; neutralizing agents; and mixtures thereof. These additives can be present in the composition according to the amounts generally used in the cosmetics and dermatological field, for example in an amount ranging from 0.01 to 50% of the total weight of the composition, for example, such as from 0.1 to 20%. The water can represent up to 70% of the total weight of the composition.

Of course, a person skilled in the art would take care to choose the optional additional additives and/or their amounts so that the advantageous properties of the composition according to the invention, namely gloss, nonstickiness, coverage and nonmigration, for example, are not, or not substantially, detrimentally affected by the envisaged addition.

The composition according to the invention can be provided in the form of a dermatological composition or of a composition for caring for the skin and/or superficial body growths or in the form of a sun protection composition, care composition for the face or body, or body hygiene composition, such as in the form of a deodorant. It can be provided in the colorless form. It can then be used as care base for the skin, superficial body growths or lips (lip balms, protecting the lips from the cold and/or the sun and/or the wind, care cream for the skin, nails or hair), a shampoo or a conditioner, or a sun protection product.

The composition of the invention can also be provided in the form of a colored product, such as for making up the skin, optionally exhibiting care or treatment properties, and can, for example, be a foundation; a blusher; a face powder; an eyeshadow; a concealer; an eyeliner or a product for making up the body; a product for making up the lips, such as a lipstick, a lip gloss or a lip pencil, optionally exhibiting care or treatment properties; or for making up the superficial body growths, such as the nails, eyelashes (in the form of, for example, a mascara), eyebrows, and hair.

Of course, the composition of the invention has to be cosmetically or dermatologically acceptable, namely comprise a nontoxic physiologically acceptable medium capable of being applied to the skin, superficial body growths or lips of the face of human beings. The term "cosmetically acceptable" is understood to mean, in accordance with the present invention, a composition with at least one of a pleasant appearance, pleasant feel, pleasant smell, and pleasant taste.

The composition may comprise at least one coloring material which is soluble in the medium which can be chosen from lipophilic dyes, hydrophilic dyes, commonly used in cosmetic or dermatological compositions, and mixtures thereof. This coloring material is generally present in an amount ranging from 0.01 to 20% of the total weight of the composition, such as of from 0.1 to 10% (if present).

The fat-soluble dyes are, for example, Sudan red, D & C Red 17, D & C Green 6, β-carotene, soybean oil, Sudan brown, D & C Yellow 11, D & C Violet 2, D & C orange 5, quinoline yellow or annatto. They can be present in an amount ranging from 0 to 20% (0.001 to 20%) of the weight of the composition, such as from 0.1 to 6% (if present). The water-soluble dyes are, for example, beetroot juice or methylene blue and can represent up to 6% of the total weight of the composition.

Use may also be made, in the composition of the invention, of at least one wax, such as those used up to the present time in cosmetics.

A wax, within the meaning of the present invention, is a lipophilic fatty compound which is solid at ambient temperature (25° C.) and atmospheric pressure (760 mmHg), which has a reversible solid/liquid state change, which has a melting temperature of greater than 40° C., for example greater than 50° C., which can range up to 200° C., and which exhibits, in the solid state, an anisotropic crystalline organization. The size of the crystals is such that the crystals diffract and/or scatter light, conferring a more or less opaque cloudy appearance on the composition. On bringing the wax to its melting temperature, it is possible to render it miscible with the oils and to form a microscopically homogeneous mixture but, on returning the temperature of the mixture to ambient temperature, recrystallization of the wax in the oils of the mixture is obtained. This recrystallization from the mixture may be responsible for the decrease in the gloss of said mixture. Consequently, the composition can comprise little or nothing in the way of conventional waxes, such as less than 20% by weight of conventional wax, or further such as less than 10% with respect to the total weight of the composition.

Conventional waxes, within the meaning of the application, are those generally used in the cosmetics and dermatological fields; they can be of natural origin, such as beeswax, candelilla wax, ouricury wax, Japan wax, cork fiber wax or sugarcane wax, paraffin or lignite waxes, microcrystalline waxes with a melting point >50° C., lanolin wax, montan wax, ozokerites, or hydrogenated oils, such as hydrogenated jojoba oil, but also of synthetic origin, such as polyethylene waxes resulting from the polymerization of ethylene and the waxes obtained by the Fischer-Tropsch synthesis with a melting point >50° C., fatty acid esters and glycerides which are solid at 50° C., or silicone waxes, such as alkyl or alkoxy poly(di)methylsiloxanes and/or poly(di) methylsiloxane esters which are solid at 50° C.

The composition of the invention can comprise little or nothing in the way of "mattifying" fillers, such as less than 5% of mattifying filler. This can be the case when it is desired to obtain a glossy layer on Keratinons substances, such as the lips, eyelashes and hair. For a foundation, on the other hand, fillers of this type may be used. A mattifying filler is generally a filler which absorbs sweat and/or sebum from the skin. Suitable non-limiting examples of such mattifying filters include silicas, talcs, clays, kaolins, polyamide (Nylon®) powders, and starch.

These fillers can be introduced in the form of a particulate paste, for example.

The composition according to the invention can be manufactured by known processes used generally in the cosmetics or dermatological field. It can, for example, be manufactured by the process which comprises heating the polymer at least to its melting temperature, in adding thereto the optional amphiphilic compound or compounds, the coloring materials soluble in the medium, the pigmentary pastes and the additives, and in then mixing the combined mixture until a clear and translucent solution is obtained. The homogeneous mixture obtained can then be poured into an appropriate mold, such as a lipstick mold, or directly into the packaging articles, such as a case or dish.

The composition of the invention can be a product for making up Keratinons substances and further can be a lipstick comprising a physiologically acceptable medium comprising a liquid fatty phase structured by at least one semi-crystalline polymer with an organic structure which is solid at ambient temperature and colored particles which are solid at ambient temperature and which are dispersed in said medium using at least one dispersing agent; the liquid fatty phase is structured by at least one semi-crystalline polymer with an organic structure which is solid at ambient temperature comprising a) a polymer backbone and b) at least one crystallizable organic side chain and/or one crystallizable organic block forming part of the polymer, said polymer having a number-average molecular mass of greater than 2,000; the liquid fatty phase and the polymer can form a medium which is physiologically acceptable for Keratinons substances, such as the lips. For example, the colored particles can be introduced into the medium in the form of a colloidal dispersion of said colored particles. This makeup product can comprise a continuous fatty phase composed of all or a portion of the structured liquid fatty phase. This makeup product can also comprise a semi-crystalline polymer with a low melting point and a compound with a high melting point as described above, such as using a second semi-crystalline polymer.

An additional aspect of the invention is a cosmetic process for caring for, making up or treating the Keratinons substances of human beings, such as the skin or the lips of the face and the superficial body growths of human beings, comprising the application, to the Keratinons substances, of the composition, such as a cosmetic composition, as defined above.

A further aspect of the invention is a process for the manufacture of a composition comprising a physiologically acceptable medium comprising at least one semi-crystalline polymer with an organic structure which is solid at ambient temperature and particles which are solid at ambient temperature and which are dispersed in said medium, wherein said process comprises introducing in said composition at least one agent for dispersing said particles.

A further aspect of the invention is the use, such as cosmetic use, of a colloidal dispersion of particles which are solid at ambient temperature in a composition, such as in a cosmetic composition, comprising a physiologically acceptable medium comprising at least one liquid fatty phase structured by at least one semi-crystalline polymer with an organic structure which is solid at ambient temperature.

Yet another aspect of the invention is the cosmetic use of a colloidal dispersion of colored particles which are solid at ambient temperature in a composition, such as in a cosmetic composition, comprising a physiologically acceptable medium comprising at least one liquid fatty phase structured by at least one semi-crystalline polymer with an organic structure which is solid at ambient temperature, as agent for coloring and/or as agent for stabilizing said composition.

An additional aspect of the invention is the cosmetic use of an agent for dispersing particles, such as colored particles, which are solid at ambient temperature in a composition, such as a cosmetic composition, comprising a physiologically acceptable medium comprising at least one liquid fatty phase structured by at least one semi-crystalline polymer with an organic structure which is solid at ambient temperature and particles which are solid at ambient temperature, such as colored particles, for producing a stable composition and/or as agent for stabilizing said composition.

As defined herein, stability involves substantially avoiding, at room temperature, i.e., 25° C., exudation of oil and flocculation and aggregation of solid particles, such as pigments and nacres.

The cosmetic composition according to the invention may exhibit treating properties. For example, the combination of a polymer with a low melting point and of a polymer with a high melting point can be used for the manufacture of a physiologically acceptable composition, and in a nonmigrating dermatological composition, for instance. Thus, it is possible to keep the composition in place where it has been deposited, and to thus improve its local action and its effectiveness.

The invention is illustrated in more detail in the following examples. The amounts are given as percentages by mass.

I) EXAMPLES OF THE MANUFACTURE OF SEMI-CRYSTALLINE POLYMERS

Example 1

Acidic Polymer with a Melting Point of 40° C.

120 g of Parleam are introduced into a 1 l reactor equipped with a central anchor stirrer, a reflux condenser and thermometer and are heated from ambient temperature to 80° C. for 45 min. The following mixture $C_1$:
40 g of cyclohexane+4 g of Triganox 141 [2,5-bis(2-ethylhexanoylperoxy)-2,5-dimethylhexane], is introduced at 80° C. over 2 h.

30 min after beginning to run in the mixture $C_1$, the mixture $C_2$, composed of:
190 g of stearyl acrylate+10 g of acrylic acid+400 g of cyclohexane, is introduced over 1 h 30.

At the end of the two additions, the reaction mixture is allowed to act for an additional 3 h at 80° C. and then all the cyclohexane present in the reaction mixture is distilled off at atmospheric pressure.

The polymer comprising 60% by weight of active material in Parleam is then obtained. Its weight-average molecular mass $M_w$ is 35 000, expressed as polystyrene equivalent, and its melting temperature M.t. is 40° C.±1° C., measured by D.S.C.

Example 2

Basic Polymer with a Melting Point of 38° C.

The same procedure is applied as in Example 1, except that N-vinylpyrrolidone is used instead of acrylic acid. The polymer obtained is at 60% by weight of active material in Parleam, its weight-average molecular mass $M_w$ is 38 000 and its M.t. is 38° C.

Example 3

Acidic Polymer with a Melting Point of 60° C.

The same procedure is applied as in Example 1, except that behenyl acrylate is used instead of stearyl acrylate. The polymer obtained is at 60% by weight of active material in Parleam. Its weight-average molecular mass $M_w$ is 42 000 and its M.t. is 60° C.

Example 4

Basic Polymer with a Melting Point of 58° C.

The same procedure is applied as in Example 2, except that behenyl acrylate is used instead of stearyl acrylate. The polymer obtained is at 60% by weight of active material in Parleam. Its molecular mass $M_w$ is 45 000 and its M.t. is 58° C.

II) COMPOSITION EXAMPLES

Example 5

Lipstick Formula

| | |
|---|---|
| 95/5 Stearyl acrylate/NVP copolymer comprising 60% of active material in Parleam according to Example 2 | 10.1% |
| Behenyl acrylate/acrylic acid copolymer comprising 60% of active material in Parleam according to Example 3 | 10.1% |
| Pigmentary paste | 17.7% |
| Hydrogenated isoparaffin (Parleam) | q.s. for 100% |

Preparation: The polymers are dissolved in a portion of the oil at 100° C. and then the addition is carried out of the pigments, milled beforehand using a triple roll mill, with a portion of the oily phase. The entire combination is mixed using a magnetic bar and then poured into lipstick molds. The pigmentary paste contains 49% of pigments (D & C Red No. 7+Yellow No. 6 (aluminum lake)+titanium dioxide), 7.5% of poly(12-hydroxystearic) acid stearate and 43.5% of Parleam, which is a hydrogenated isoparaffin (6–8 mol of isobutylene).

The pigmentary paste is obtained using a disperser-mill of Dispermat type and heating the Parleam at 25–30° C. for approximately 30 minutes. It is stable for at least 3 months at ambient temperature, that is to say that no sedimentation is observable even with stirring.

A stick of lipstick is obtained which has a hardness of 117 gf, measured by the "cheese wire" method. The lipstick obtained is glossy, nonsticky and nonmigrating. This was confirmed by a comparative sensory test on a panel of experts, by half-lips, with a glossy product of the prior art Rouge Absolu from Lancôme. The lipstick of the invention was judged to be as glossy on application as that of the prior art by all the testers, with much slighter migration. In addition, no flocculation or aggregation of the pigments was observed. The makeup of the lips obtained is uniform and covering.

Example 6

Lipstick Formula

| | |
|---|---|
| Copolymer according to Example 3 | 12.5% |
| Copolymer according to Example 1 | 12.5% |
| Pigmentary paste | 17.7% |
| Hydrogenated isoparaffin | q.s. for 100% |

The composition of the pigmentary paste is identical to that of Example 5.

This lipstick in the form of a stick was prepared as in Example 5. It is glossy, nonsticky, uniform, covering and nonmigrating. It was judged by a panel of experts in comparison with a lipstick of the prior art Rouge Magnetique from Lancôme, regarded as not very migrating. The lipstick of the invention was judged to be glossier than Rouge Magnetique for comparable properties of nonmigration. In addition, no flocculation or aggregation of the pigments was observed.

The lipstick of the prior art, Rouge Absolu and Rouge Magnétique, do not comprise semi-crystalline polymers based on melting point, in combination in particular with a crystalline or semi-crystalline compound with a high melting point.

Example 7

Lipstick Formula

It differs from Example 5 by the use of a polyethylene wax (Performalen 500, sold by Petrolite), with a melting point of 83° C. to within about 1° C., instead of the polymer of Example 3. The cosmetic properties obtained are comparable to those of the formula of Example 5.

Example 8

Lipstick Formula

| | |
|---|---|
| Engage 8400 | 10.0% |
| Copolymer of Example 1 | 10.1% |
| Pigmentary paste | 17.7% |
| Hydrogenated liquid paraffin | q.s. for 100% |

The pigmentary paste is identical to that of Example 5.
The manufacture of this lipstick as a stick is identical to that of Example 5.

Example 9

Lipstick Formula

| | |
|---|---|
| Stearyl acrylate/acrylic acid (95/5) copolymer comprising 50% of active material in Parleam | 25% |
| Behenyl acrylate/N-vinylpyrrolidone (95/5) copolymer comprising 62.5% of active material in Parleam | 25% |
| Solsperse 21000 (poly(12-hydroxystearic acid) | 2% |
| Pigments | 8.66% |
| Hydrogenated isoparaffin | q.s. for 100% |

Preparation: the polymers are dissolved in a portion of the oil at 100° C. and then the addition is carried out of the pigments, which were milled beforehand using a triple roll mill, with a portion of the oily phase. The entire combination is mixed using a magnetic bar and is then poured into lipstick molds. The pigments are in accordance with Example 5.

A stick of lipstick is obtained which has a hardness of 227 gf±20 gf, measured by the "cheese wire" method, is nonmigrating, is nonsticky, is easily deposited on the lips and gives a satiny layer.

Example 10

Lipstick Formula

| | |
|---|---|
| Behenyl methacrylate/acrylic acid (95/5) copolymer at 50% in Parleam | 25% |
| Behenyl acrylate/N-vinylpyrrolidone (95/5) copolymer at 62.5% in Parleam | 25% |
| Solsperse 21000 (poly(12-hydroxystearic acid) | 2% |
| Pigments | 8.66% |
| Hydrogenated isoparaffin | q.s. for 100% |

Preparation: the polymers are dissolved in a portion of the oil at 100° C. and then the addition is carried out of the pigments, which were milled beforehand using a triple roll mill, with a portion of the oily phase. The entire combination is mixed using a magnetic bar and is then poured into lipstick molds. The pigments are in accordance with Example 5.

A stick of lipstick is obtained which has a hardness of 342 gf±20 gf, measured by the "cheese wire" method, is nonmigrating, is nonsticky, is easily deposited on the lips and gives a satiny layer.

What is claimed is:

1. A composition comprising, in a physiologically acceptable medium:
    (i) at least one liquid fatty phase structured by at least two semi-crystalline polymers having an organic structure, wherein the first semi-crystalline polymer is chosen from polymers having a melting temperature, $M.p._1$, of at least equal to 50° C. and the second semi-crystalline polymer is chosen from polymers having a melting temperature, $M.p._2$, of less than 50° C., and wherein said semi-crystalline polymers are solid at ambient temperature;
    (ii) particles that are solid at ambient temperature, wherein the particles are introduced into the medium in the form of a colloidal dispersion of the particles; and
    (iii) at least one dispersing agent in an amount sufficient to disperse said particles in said medium.

2. The composition of claim 1, wherein the particles are chosen from pigments, pearlescent agents, fillers, and mixtures thereof.

3. The composition of claim 1, wherein the particles are colored particles.

4. The composition of claim 1, wherein the colloidal dispersion is present in an amount ranging from 0.5% to 60% by weight, relative to the total weight of the composition.

5. The composition of claim 4, wherein the colloidal dispersion is present in an amount ranging from 2% to 40% by weight, relative to the total weight of the composition.

6. The composition of claim 1, wherein the at least one dispersing agent represents from 0.3 mg/m$_2$ to 5 mg/m$_2$ of the particle surface area.

7. The composition of claim 6, wherein the at least one dispersing agent represents from 0.5 mg/m$_2$ to 4 mg/m$_2$ of the particle surface area.

8. The composition of claim 1, wherein the at least one dispersing agent is chosen from the stearate of poly(12-hydroxystearic acid), poly(12-hydroxystearic acid), and polyglyceryl-2 dipolyhydroxystearate.

9. The composition of claim 1, wherein the colloidal dispersion comprises a fatty substance that is liquid at ambient temperature and forms part of the liquid fatty phase.

10. The composition of claim 1, wherein at least one semi-crystalline polymer has a number-average molecular mass of greater than 2,000.

11. The composition of claim 10, wherein at least one semi-crystalline polymer has a number-average molecular mass ranging from 3,000 to 500,000.

12. The composition of claim 11, wherein at least one semi-crystalline polymer has a number-average molecular mass ranging from 4,000 to 99,000.

13. The composition of claim 1, wherein at least one semi-crystalline polymer comprises
    (i) a polymer backbone; and
    (ii) at least one crystallizable organic side chain; and/or at least one crystallizable organic block which forms part of the polymer backbone of said at least one semi-crystalline polymer.

14. The composition of claim 1, wherein at least one semi-crystalline polymer is soluble in the liquid fatty phase at a temperature greater than its melting temperature.

15. The composition of claim 1, wherein said composition is applied to a Keratinons substrate.

16. The composition of claim 15, wherein the second semi-crystalline polymer has a melting temperature greater than the temperature of the Keratinons substrate.

17. The composition of claim 16, wherein the Keratinons substrate is skin or lips.

18. The composition of claim 1, wherein at least one semi-crystalline polymer is chosen from:
    block copolymers of polyolefins with controlled crystallization;
    aliphatic and aromatic polyester polycondensates; aliphatic/aromatic copolyesters; and
    homo- and copolymers carrying at least one crystallizable side chain.

19. The composition of claim 1, wherein at least one semi-crystalline polymer is chosen from homopolymers and copolymers comprising from 50% to 100% by weight of units resulting from polymerization of at least one monomer carrying at least one crystallizable hydrophobic side chain.

20. The composition of claim 1, wherein at least one semi-crystalline polymer is chosen from homopolymers and copolymers resulting from the polymerization of at least one monomer having at least one crystallizable chain of formula X:

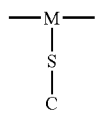

wherein M represents an atom of the polymer backbone, S represents a spacer, C represents a crystallizable group, and "S—C" represents an optionally fluorinated or perfluorinated alkyl chain comprising at least 11 carbon atoms.

21. The composition of claim 1, wherein at least one semi-crystalline polymer is chosen from polymers resulting from the polymerization of at least one monomer chosen from acrylic acid, methacrylic acid, crotonic acid, itaconic acid, maleic acid, and maleic anhydride.

22. The composition of claim 1, wherein at least one semi-crystalline polymer is chosen from homopolymers and copolymers resulting from the polymerization of at least one monomer having a crystallizable chain chosen from saturated $C_{14}$–$C_{24}$ alkyl(meth)acrylates; $C_{11}$–$C_{15}$ perfluoroalkyl (meth)acrylates; N-($C_{14}$ to $C_{24}$ alkyl(meth)acrylamides unsubstituted or substituted with at least one fluorine atom vinyl esters comprising chains chosen from $C_{14}$ to $C_{24}$ alkyl and peifluoroalkyl chains; vinyl ethers comprising chains chosen from $C_{14}$ to $C_{24}$ alkyl and perfluoroalkyl chains; $C_{14}$ to $C_{24}$ αolefins; and para-alkylstyrenes comprising an alkyl group comprising from 12 to 24 carbon atoms.

23. The composition of claim 1, wherein at least one semi-crystalline polymer is chosen from homopolymers of alkyl(meth)acrylate, wherein said alkyl is chosen from $C_{14}$ to $C_{24}$ alkyl groups, and copolymers of alkyl (meth)acrylate, wherein said alkyl is chosen from $C_{14}$ to $C_{24}$ alkyl groups, and of alkyl(meth)acrylamide, wherein said alkyl is chosen from $C_{14}$ to $C_{24}$ alkyl groups, with a hydrophilic monomer.

24. The composition of claim 1, wherein at least one semi-crystalline polymer is chosen from copolymers of alkyl (meth)acrylate, wherein said alkyl is chosen from $C_{14}$ to $C_{24}$ alkyl groups, and of alkyl(meth)acrylamide, wherein said alkyl is chosen from $C_{14}$ to $C_{24}$ alkyl groups, with a hydrophilic monomer that is not identical to (meth)acrylic acid.

25. The composition of claim 24, wherein the hydrophilic monomer is chosen from N-vinylpyrrolidone, hydroxyethyl (meth)acrylate, and mixtures thereof.

26. The composition of claim 1, wherein at least one semi-crystalline polymer is present in an amount ranging from 0.1% to 80% by weight, relative to the total weight of the composition.

27. The composition of claim 26, wherein at least one semi-crystalline polymer is an amount ranging from 0.5% to 40% by weight, relative to the total weight of composition.

28. The composition of claim 1, wherein at least one semi-crystalline polymer is present in an amount greater than 10% by weight, relative to the total weight of the composition.

29. The composition of claim 1, wherein the first polymer has a melting temperature, M.p.$_1$, ranging from greater than or equal to 55° C. to less than or equal to 150° C.

30. The composition of claim 29, wherein the first polymer has a melting temperature, M.p.$_1$, ranging from greater than or equal to 60° C. to less than or equal to 130° C.

31. The composition of claim 1, wherein the second polymer has a melting temperature, $M.p._2$, ranging from greater than or equal to 30° C. to less than 50° C.

32. The composition of claim 1, wherein the at least one liquid fatty phase is present in an amount ranging from 5% to 99% by weight, relative to the total weight of the composition.

33. The composition of claim 32, wherein the at least one liquid fatty phase is p resent in an amount ranging from 20% to 80% by weight, relative to the total weight of the composition.

34. The composition of claim 1, wherein the at least one fatty phase comprises at least one hydrocarbonaceous oil chosen from mineral and synthetic origins.

35. The composition of claim 1, wherein said composition is for caring for and/or treating and/or making up a Keratinons substance.

36. The composition of claim 1, further comprising at least one coloring material that is soluble in the medium and is chosen from lipophilic dyes and hydrophilic dyes.

37. The composition of claim 1, further comprising at least one additive chosen from mattifying fillers, water, antioxidants, essential oils, preservatives, neutralizing agents, fragrances, waxes, and pasty fatty substances.

38. The composition of claim 37, comprising at least one wax in an amount of less than 20% by weight, and at least one mattifying filler in an amount less than 5% by weight, of the total weight of said composition.

39. The composition of claim 1, wherein the at least one liquid fatty phase represents the continuous phase of the composition.

40. The composition of claim 1, wherein said composition is in anhydrous form.

41. The composition of claim 1, wherein said composition is in cast form.

42. The composition of claim 1, wherein said composition is provided in a form chosen from mascara, eyeliner, foundation, lipstick, deodorant, product for making up the body, eyeshadow, face powder, and concealer.

43. A product for making up a Keratinons substance comprising, in a physiologically acceptable medium, (i) at least one liquid fatty phase structured by at least two semi-crystalline polymers having an organic structure, wherein the first semi-crystalline polymer is chosen from polymers having a melting temperature, $M.p._1$, of at least equal to 50° C., and wherein the second semi-crystalline polymer is chosen from polymers having a melting temperature, $M.p._2$, of less than 50° C., and wherein said semi-crystalline polymer is solid at ambient temperature; (ii) colored particles that are solid at ambient temperature and (iii) at least one dispersing agent in an amount sufficient to disperse said colored particles in said medium.

44. The product of claim 43, wherein the colored particles are introduced into the medium in the form of a colloidal dispersion of said colored particles.

45. The product of claim 43, wherein at least one semi-crystalline polymer comprises a) a polymer backbone; and b) at least one crystallizable organic side chain, and has a number-average molecular mass of greater than 2,000.

46. The product of claim 43, wherein said product is in a solid stick form having a hardness ranging from 100 gf to 350 gf.

47. A cosmetic process for caring for, making up, or treating a Keratinons substance of a human being, comprising applying to said Keratinons substance an effective amount of a composition comprising, in a physiologically acceptable medium:
(i) at least one liquid fatty phase structured by at least two semi-crystalline polymeru having an organic structure, wherein the first semi-crystalline polymer is chosen from polymers having a melting temperature, $M.p._1$, of at least equal to 50° C. and the second semi-crystalline polymer is chosen from polymers having a melting temperature, $M.p._2$, of less than 50° C., and wherein said semi-crystalline polymers are solid at ambient temperature; and
(ii) particles that are solid at ambient temperature; and
(iii) at least one dispersing agent in an amount sufficient to disperse said particles in said medium.

48. A process of making a cosmetic composition comprising a physiologically acceptable medium, comprising including in said medium (i) at least two semi-crystalline polymers that have an organic structure and are solid at ambient temperature, wherein the first semi-crystalline polymer is chosen from polymers having a melting temperature, $M.p._1$, of at least equal to 50° C. and the second semi-crystalline polymer is chosen from polymers having a melting temperature, $M.p._2$, of less than 50° C., and (ii) particles that are solid at ambient temperature and are dispersed in said medium; and (iii) at least one dispersing agent in an amount effective to disperse said particles in said medium.

49. A process of using a colloidal dispersion of solid particles in a cosmetic composition comprising, in a physiologically acceptable medium, at least one liquid fatty phase by at least two semi-crystalline polymers, wherein the first semi-crystalline polymer is chosen from polymers having a melting temperature, $M.p._1$, of at least equal to 50° C., and the second semi-crystalline polymer is chosen from polymers having a melting temperature, $M.p._2$, of less than 50° C., and, and wherein said semi-crystalline polymers have an organic structure and are solid at ambient temperature, comprising including in said cosmetic composition a colloidal dispersion of particles with at least one dispersing agent in an amount sufficient to disperse said particles in said medium wherein the particles are solid at ambient temperature.

50. A process for coloring and/or stabilizing a cosmetic composition comprising, in a physiologically acceptable medium, at least one liquid fatty phase structured by at least two semi-crystalline polymers, wherein the first semi-crystalline polymer is chosen from polymers having a melting temperature, $M.p._1$, of at least equal to 50° C., and the second semi-crystalline polymer is chosen from polymers having a melting temperature, $M.p._2$, of less than 50° C., said semi-crystalline polymers having an organic structure and being solid at ambient temperature, comprising including in said cosmetic composition a colloidal dispersion of colored particles that are solid at ambient temperature wherein said dispersion comprises at least one dispersing agent in an amount sufficient to disperse said particles in said medium.

51. A method for stabilizing a cosmetic composition and/or producing a stable cosmetic composition comprising:
including, in a cosmetic composition comprising, in a physiologically acceptable medium, at least one liquid fatty phase structured by at least two semi-crystalline polymers that have an organic structure and are solid at ambient temperature, wherein the first semi-crystalline polymer is chosen from polymers having a melting temperature, $M.p._1$, of at least equal to 50° C., and the second semi-crystalline polymer is chosen from polymers having a melting temperature, $M.p._2$, of less than 50° C., colored particles that are solid at ambient temperature, and a dispersing agent in an amount effective for dispersing said colored particles.

52. A composition comprising, in a physiologically acceptable medium:
   (i) at least one liquid fatty phase structured by at least two semi-crystalline polymers that have an organic structure, wherein the first semi-crystalline polymer is chosen from polymers having a melting temperature, $M.p._1$, of at least equal to 50° C., and the second semi-crystalline polymer is chosen from polymers having a melting temperature, $M.p._2$, of less than 50° C., and wherein said semi-crystalline polymer is solid at ambient temperature; and
   (ii) particles that are solid at ambient temperature, wherein the particles are introduced into the medium in the form a colloidal dispersion of the particles; and
   (iii) at least one dispersing agent in an amount sufficient to disperse said particles in said medium;
   wherein said semi-crystalline polymers do not comprise a polysaccharide backbone.

53. The composition of claim 1, wherein at least one semi-crystalline polymer is chosen from block copolymers comprising at least one crystallizable block and at least one amorphous block and from homopolymers and copolymers comprising at least one crystallizable side chain per repeat unit.

54. The composition of claim 53, wherein in said block copolymers, there are at least two crystallizable blocks that are not identical and/or there are at least two amorphous blocks that are not identical.

55. The composition of claim 1, wherein at least one semi-crystalline polymer results from a monomer having a crystallizable chain chosen from saturated $C_{14}$ to $C_{22}$(meth)acrylates.

56. The composition of claim 13, wherein the at least one crystallizable organic side chain and at least one crystallizable organic block represent at least 30% of the total weight of the said at least one semi-crystalline polymer.

57. The composition of claim 1, wherein the weight ratio of at least one semi-crystalline polymer to said at least one liquid fatty phase ranges from 0.20:1 to 0.50:1.

58. The composition of claim 57, wherein said weight ratio ranges from 0.25:1 to 0.45:1.

59. A lipstick comprising, in a physiologically acceptable medium:
   (i) at least one liquid fatty phase structured by at least two semi-crystalline polymer having an organic structure, wherein the first semi-crystalline polymer is chosen from polymers having a melting temperature, $M.p._1$, of at least equal to 50° C., and the second semi-crystalline polymer is chosen from polymers having a melting temperature, $M.p._2$, of less than 50° C., and wherein said semi-crystalline polymers are solid at ambient temperature; and
   (ii) particles that are solid at ambient temperature; and
   (iii) at least one dispersing agent in an amount sufficient to disperse said particles in said medium.

60. A process for stabilizing a cosmetic composition comprising, in a physiologically acceptable medium, at least one liquid fatty phase structured by at least two semi-crystalline polymers, said semi-crystalline polymers having an organic structure and being solid at ambient temperature, wherein the first semi-crystalline polymer is chosen from polymers having a melting temperature, $M.p._1$, of at least equal to 50° C., and the second semi-crystalline polymer is chosen from polymers having a melting temperature, $M.p._2$, of less than 50° C., and particles that are solid at ambient temperature, wherein the particles are introduced into the medium in the form of a colloidal dispersion of the particles comprising including in said cosmetic composition an effective amount of a dispersing agent.

61. The process of claim 60, wherein said particles are colored particles.

62. A process for dispersing in a cosmetic composition particles that are solid at ambient temperature, wherein said composition comprises, in a physiologically acceptable medium at least one liquid fatty phase structured by at least two semi-crystalline polymers, said semi-crystalline polymers having an organic structure and being solid at ambient temperature, wherein the first semi-crystalline polymer is chosen from polymers having a melting temperature, $M.p._1$, of at least equal to 50° C. and the second semi-crystalline polymer is chosen from polymers having a melting temperature, $M.p._2$, of less than 50° C., and particles that are solid at ambient temperature, wherein the particles are introduced into the medium in the form of a colloidal dispersion of the particles,
   comprising including in said cosmetic composition an effective amount of a dispersing agent for said particles.

63. The process of claim 62, wherein said particles are colored particles.

* * * * *

UNITED STATES PATENT AND TRADEMARK OFFICE
CERTIFICATE OF CORRECTION

PATENT NO.         : 7,129,276 B2                                                Page 1 of 1
APPLICATION NO. : 10/138326
DATED              : October 31, 2006
INVENTOR(S)        : Véronique Ferrari It is certified that error appears in the above-identified patent and that said Letters Patent is hereby corrected as shown below:

Claim 6, col. 21, line 10, "mg/m$_2$" should read -- mg/m$^2$ -- both instances.

Claim 7, col. 21, line 14, "mg/m$_2$" should read -- mg/m$^2$ -- both instances.

Claim 15, col. 21, line 47 "Keratinons" should read -- keratinous --.

Claim 16, col. 21, line 50 "Keratinons" should read -- keratinous --.

Claim 17, col. 21, line 51 "Keratinons" should read -- keratinous --.

Claim 22, col. 22, line 33, insert space between "α" and -- olefins --.

Claim 22, col. 22, line 31, "peifluoroalkyl" should read -- perfluoroalkyl --.

Claim 33, col. 23, line 10, delete space in "p resent".

Claim 35, col. 23, line 18, "Keratinons" should read -- keratinous --.

Claim 43, col. 23, line 45, "Keratinons" should read -- keratinous --.

Claim 47, col. 24, line 7, "polymeru" should read -- polymers --.

Claim 49, col. 24, line 38, delete "and" second instance.

Signed and Sealed this

Twenty-seventh Day of February, 2007

JON W. DUDAS
*Director of the United States Patent and Trademark Office*